US00PP30921P2

(12) United States Plant Patent
Van Dijk

(10) Patent No.: US PP30,921 P2
(45) Date of Patent: Oct. 1, 2019

(54) ***ANTHURIUM* PLANT NAMED 'ANTHFRAXK'**

(50) Latin Name: ***Anthurium andraeanum* L.**
Varietal Denomination: ANTHFRAXK

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,539

(22) Filed: Mar. 13, 2018

(51) Int. Cl.
*A01H 5/02* (2018.01)

(52) U.S. Cl.
USPC ..... Plt./366

(58) Field of Classification Search
USPC ..... Plt./366
CPC ..... A01H 5/02
See application file for complete search history.

*Primary Examiner* — Keith O. Robinson
(74) *Attorney, Agent, or Firm* — Jondle & Associates, P.C.

(57) ABSTRACT

A new *Anthurium* plant named 'ANTHFRAXK' particularly distinguished by having shiny, white, cordate and durable spathes that retain the original color for a very long period of time, dark green and elliptical cordate, durable leaves, white spadix with light yellow tips, early and rich flowering continuously through the year, and a plant height of 45.0 cm to 50.0 cm is disclosed.

3 Drawing Sheets

Genus and species: *Anthurium andraeanum* L.
Variety denomination: 'ANTHFRAXK'.

BACKGROUND OF THE NEW PLANT

The present invention comprises a new and distinct variety of *Anthurium*, botanically known as *Anthurium andraeanum* L., and hereinafter referred to by the variety name 'ANTHFRAXK'. The new *Anthurium* plant is a product of a planned breeding program conducted by the inventor in Bleiswijk, the Netherlands. The objective of this breeding program was to create a new 45.0 cm to 50.0 cm height plant with shiny blistered, white, cordate and durable spathes.

The new variety originated from a cross-pollination made in October 2009 in Bleiswijk, The Netherlands. The female parent was a white *Anthurium* pot plant designated '18667-01' (unpatented), and the male parent was a pink *Anthurium* pot plant designated '18769-01' (unpatented).

A single plant was selected from the progeny of the stated cross in March 2012 and has been asexually reproduced repeatedly by tissue culture in Bleiswijk, The Netherlands over a 5-year period. The present invention has been found to retain its distinctive characteristics through successive asexual propagations.

Plant Breeder's Rights for this variety have been applied for in the European Union on Nov. 24, 2015. 'ANTHFRAXK' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny and blistered, white, cordate spathes;
2) White spadix with yellow tips;
3) Older flowers remain white longer; and
4) The plant develops many shoots.

DESCRIPTION OF THE PHOTOGRAPHS

This new *Anthurium* plant is illustrated by the accompanying photographs which show the overall plant habit including blooms, bud and foliage of the plant; the colors shown are as true as can be reasonably obtained by conventional photographic procedures. The photographs are of a 52-week old plant grown in a greenhouse in Bleiswijk, The Netherlands in December 2017. Colors in the photographs may differ from the color values cited in the detailed botanical description, which accurately describe the actual colors of the new variety.

DESCRIPTION OF THE NEW VARIETY

Figure 1:
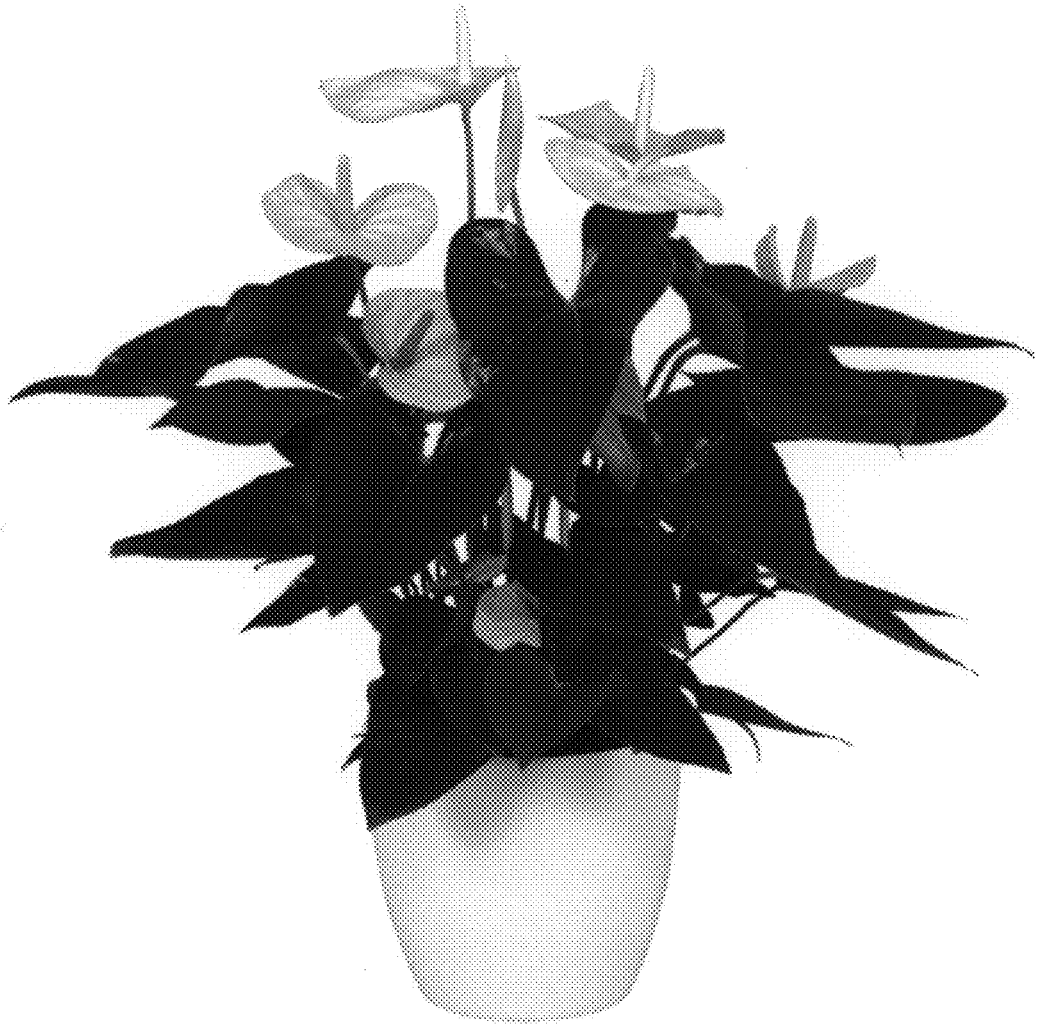
FIG. 1 shows the overall plant habit, including blooms, bud and foliage.
Figure 2:
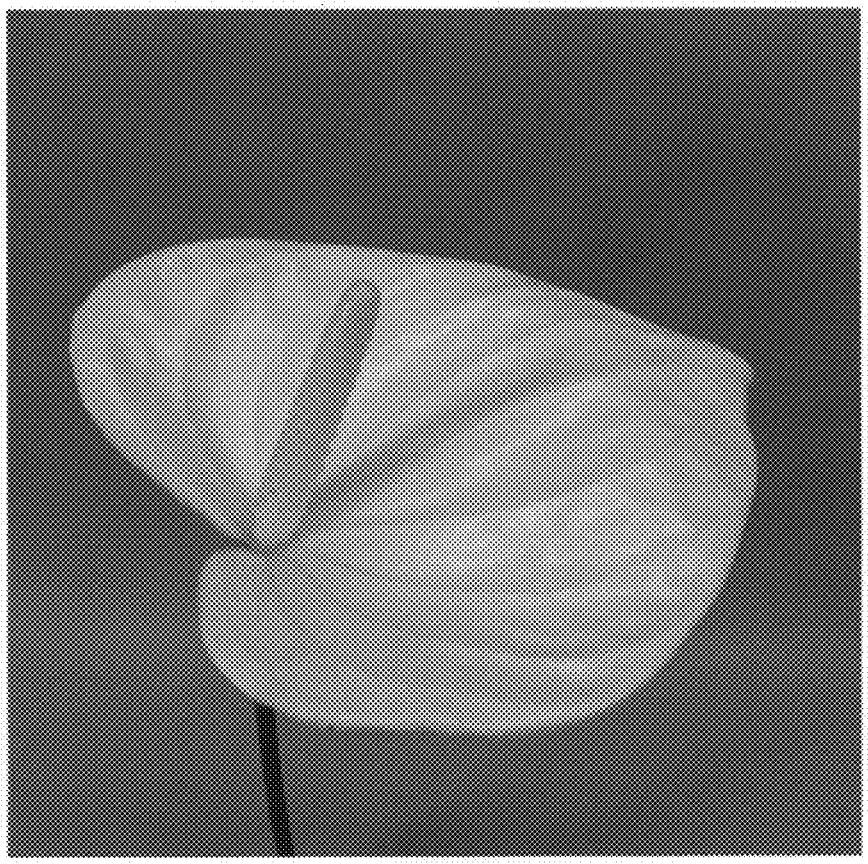
FIG. 2 shows a close-up of the mature spathe.
Figure 3:
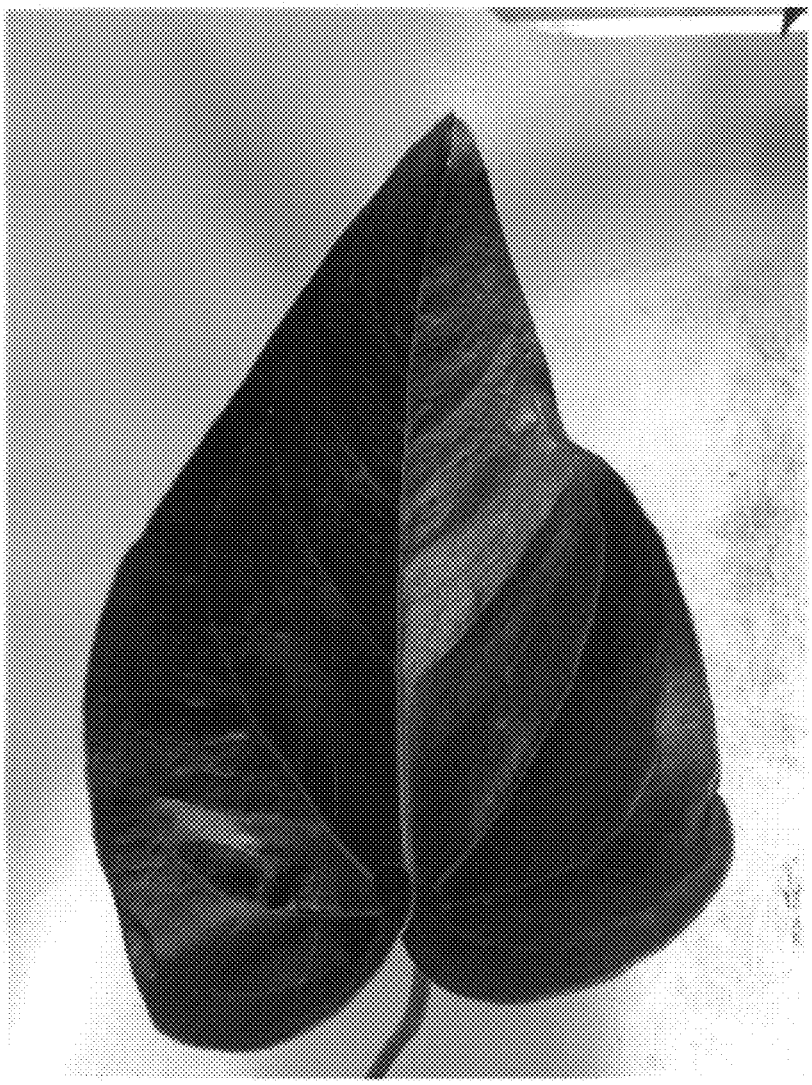
FIG. 3 shows a close-up of the upper leaf blade surface.

The following detailed description sets forth the distinctive characteristics of 'ANTHFRAXK'. The data which define these characteristics were collected from asexual reproductions carried out in Bleiswijk, The Netherlands. The plant history was taken on 52-week old plants which were planted from tissue culture in 17 centimeter (diameter) pots and grown in a glass greenhouse between 19° C. and 24° C. Observations were made in December 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFRAXK'.

Parentage:

*Female parent*.—*Anthurium* plant '18667-01' (unpatented).

*Male parent*.—*Anthurium* plant '18769-01' (unpatented).

Plant:

*Propagation*.—Tissue culture.

*Root description*.—Fleshy-creamy (RHS 160D) colored roots with small hairy lateral roots having yellow (RHS 13A) colored root tips.

*Time to produce a finished flowering plant*.—50 to 54 weeks after planting in a 17 cm (diameter) pot.

*Growth habit*.—Upright, widespread.

*Height* (*measured from soil, including inflorescence*) .—45.0 cm to 50.0 cm.

*Width* (*measured from leaf tips*).—55.0 cm to 60.0 cm.

Leaves:

*Immature leaves*.—Length: 18.0 cm to 20.0 cm. Width: 10.0 cm to 12.0 cm. Color: Upper surface: RHS 144A. Lower surface: RHS 146B. Texture (both upper and lower surfaces): Shiny, leathery, thin and soft.

*Mature leaves*.—Length (fully expanded): 24.0 cm to 26.0 cm. Width: 13.0 cm to 15.0 cm. Shape: Elliptical cordate. Apex: Obtuse. Base: Cordate. Leaf blade angle with the petiole: Between 120 degrees and 140 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 144C.

*Lobes*.—Present. Arrangement: Leaf blade has two lobes extending past the petiole. The lobes are non-touching. Length of lobes of mature leaf blades: 4.5 cm to 5.5 cm. Width of lobes of mature leaf blades: 5.5 cm to 6.5 cm. Distance from petiole/leaf junction to highest point on lobes of mature leaf: 5.0 cm to 6.0 cm.

*Petiole*.—Cross-section: Round. Diameter: 0.4 cm to 0.5 cm. Length: 31.0 cm to 33.0 cm for a mature leaf size. Color: Mature leaf: RHS 144A. Immature leaf: RHS 144B. Cataphyll color surrounding the petiole: Outside: RHS 144B. Inside: RHS 144C.

*Geniculum*.—Length: 3.0 cm to 3.5 cm. Width: 0.5 cm to 0.6 cm. Color: RHS 144B.

Inflorescence:

*Arrangement*.—Single.

*Flowering habit* (*length of flowering season*).—Continuous.

*Number of inflorescences per plant*.—4 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 110 degrees and 120 degrees; the spathe stands on a wiry peduncle about 3.0 cm to 6.0 cm above the foliage.

*Shape*.—Cordate.

*Apex*.—Mucronate.

*Base*.—Cordate.

*Texture*.—Shiny and blistered.

*Blistering*.—Medium to weak.

*Margin*.—Slightly undulated.

*Size*.—Length: 11.5 cm to 12.5 cm. Width: 11.0 cm to 12.0 cm.

*Lobes*.—Present.

*Arrangement*.—The spathe has two lobes extending past the peduncle. The lobes are non-touching. Length: 1.5 cm to 2.5 cm. Width: 4.5 cm to 5.5 cm.

*Color*.—Just fully open: Upper surface: RHS NN155B. Lower surface: RHS NN155B. This white color remains for a very long period, at least more than 30 weeks after opening.

Peduncle:

*Shape*.—Erect.

*Cross-section*.—Round.

*Length*.—38.0 cm to 41.0 cm.

*Diameter*.—0.4 cm to 0.5 cm.

*Color*.—RHS 144B/C.

Flowering time:

*General*.—One small, rooted, untreated tissue culture plant of 8.0 cm tall will flower, depending on the season, after 50 to 52 weeks and 4 to 5 blossoms appear. More blossoms appear after some additional weeks so that a full flowering and commercial plant will have 6 to 7 white spathes. Smaller blossoms may occur on immature plants.

Spadix:

*Size*.—Length: 5.0 cm to 6.0 cm (depending on flower size). Width (at apex): 0.6 cm to 0.7 cm. Width (at base): 0.7 cm to 0.8 cm.

*Shape*.—Columnar.

*Angle from spadix tip to peduncle*.—170 degrees to 180 degrees.

*Curvature of the longitudinal axis*.—Straight to weakly incurved.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 10A. Mature: RHS NN155A. Ages to: RHS 144A/B.

Flowers:

*Quantity per spadix*.—150 to 200.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: 150 to 200. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions.

COMPARISON WITH PARENTAL AND COMMERCIAL VARIETIES

The female parent of 'ANTHFRAXK', cultivar '18667-01' (unpatented), is no longer in existence, so a meaningful comparison cannot be made.

'ANTHFRAXK' differs from the male parent plant '18769-01' (unpatented) in that 'ANTHFRAXK' has white spathes, green cataphylls, and spadix that are white at the base and yellow at the top, whereas '18769-01' has pink spathes, cataphylls that are a mix of green and red, and spadix that are light pink at the base and dark orange at the top.

'ANTHFRAXK' differs from similar commercial variety 'ANTHURWAP' (unpatented) in that 'ANTHFRAXK' has green cataphylls, creamy colored roots, green immature leaves, and high shoot development, whereas 'ANTHURWAP' has pink cataphylls, light pink colored roots, immature leaves that are a mix of dark green and light purple, and medium shoot development. Additionally, 'ANTHFRAXK' has a smaller distance from the petiole/leaf junction to the highest point on the lobes of mature leaves than 'ANTHURWAP'.

'ANTHFRAXK' differs from similar commercial variety 'ANTHERZEK' (U.S. Plant Pat. No. 28,327) in that 'ANTHFRAXK' has high shoot development, whereas 'ANTHERZEK' has medium shoot development. Additionally, 'ANTHFRAXK' has a taller plant and a larger distance from the petiole/leaf junction to the highest point on the lobes of mature leaves than 'ANTHERZEK'.

I claim:

1. A new and distinct variety of *Anthurium* plant named 'ANTHFRAXK', substantially as illustrated and described herein.

* * * * *